(12) United States Patent
Biro et al.

(10) Patent No.: US 8,302,238 B2
(45) Date of Patent: Nov. 6, 2012

(54) MOTORIZED TOOTHBRUSH TIP HAVING INNER AND OTHER HEADS COUNTER AROUND DIFFERENT AXES

(75) Inventors: Ladislau Biro, Middlesex County, NJ (US); Howard Cohen, Hudson County, NJ (US)

(73) Assignee: East Coast Medical & Dental Devices, Inc., Hoboken, NJ (US)

( * ) Notice: Subject to any disclaimer, the term of this patent is extended or adjusted under 35 U.S.C. 154(b) by 627 days.

(21) Appl. No.: 12/460,625

(22) Filed: Jul. 22, 2009

(65) Prior Publication Data
US 2011/0016647 A1    Jan. 27, 2011

(51) Int. Cl.
*A46B 13/02* (2006.01)
(52) U.S. Cl. .................... 15/22.1; 15/22.2; 15/28
(58) Field of Classification Search ..... 15/28, 21.1–22.4
See application file for complete search history.

(56) References Cited

U.S. PATENT DOCUMENTS

| | | | |
|---|---|---|---|
| 5,416,942 A | 5/1995 | Baldacci et al. | |
| 5,850,655 A | 12/1998 | Gocking et al. | |
| 5,974,613 A | 11/1999 | Herzog | |
| 6,032,313 A * | 3/2000 | Tsang | 15/22.1 |
| 6,349,442 B1 | 2/2002 | Cohen et al. | |
| 6,665,901 B2 | 12/2003 | Driesen et al. | |
| 6,751,823 B2 * | 6/2004 | Biro et al. | 15/22.1 |
| 6,957,468 B2 | 10/2005 | Driesen et al. | |
| 7,146,675 B2 | 12/2006 | Ansari et al. | |
| 7,392,562 B2 | 7/2008 | Boland et al. | |
| 7,788,756 B2 * | 9/2010 | Kraemer | 15/28 |
| 2003/0066145 A1 * | 4/2003 | Prineppi | 15/22.1 |

* cited by examiner

*Primary Examiner* — Shay Karls
(74) *Attorney, Agent, or Firm* — Howard C. Miskin; Gloria Tsui-Yip

(57) ABSTRACT

A toothbrush tip for a motorized toothbrush with a first brush head and a second brush head. The second brush head encircles the first brush head. The first and second brush heads has different axes of rotation. The first and second brush heads are driven by an elongated shaft. The shaft engages the second brush head. Interactive gear teeth associated with each first and second brush heads allows the first and second brush heads to rotate at opposite direction, upon being driven by the shaft.

43 Claims, 19 Drawing Sheets

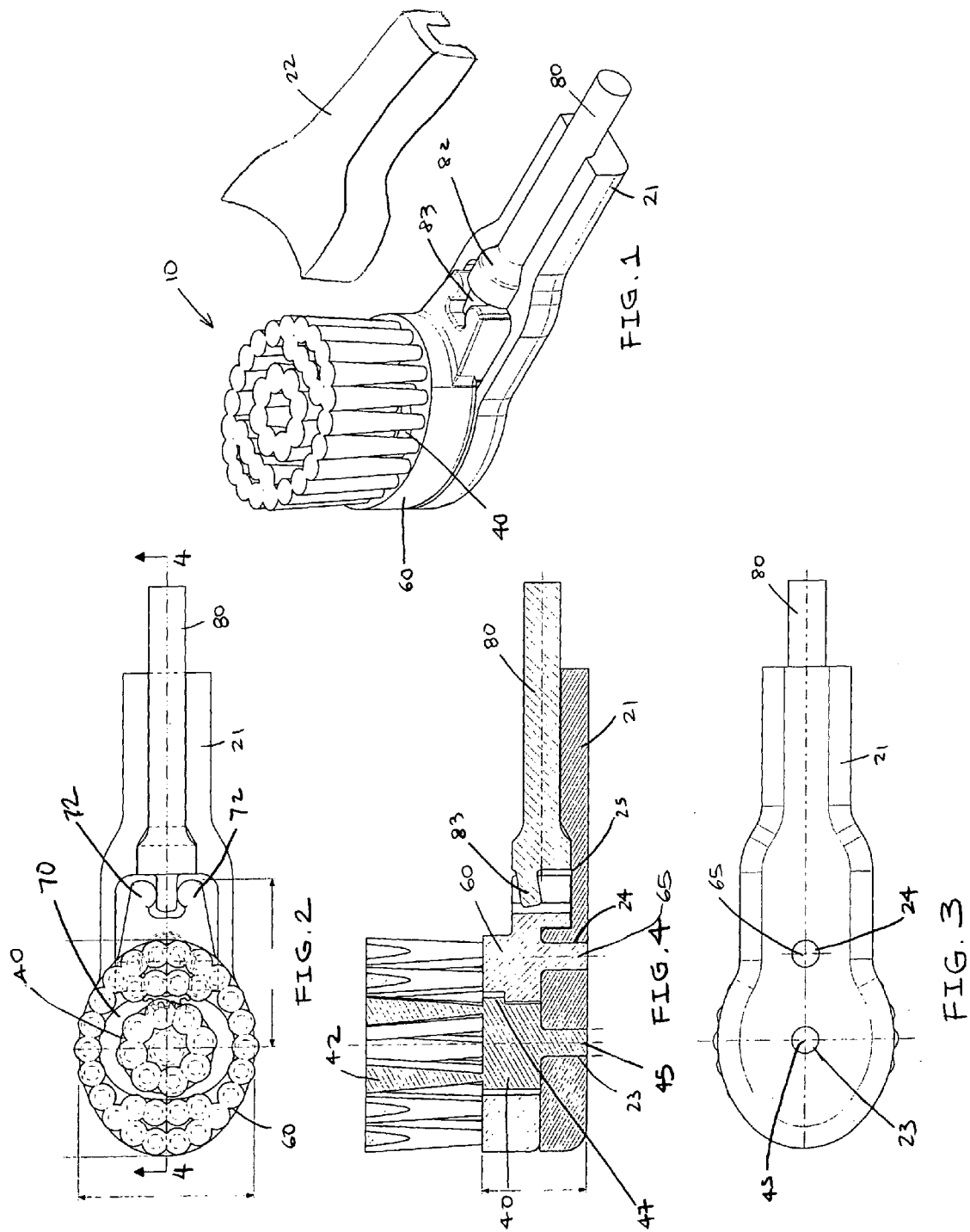

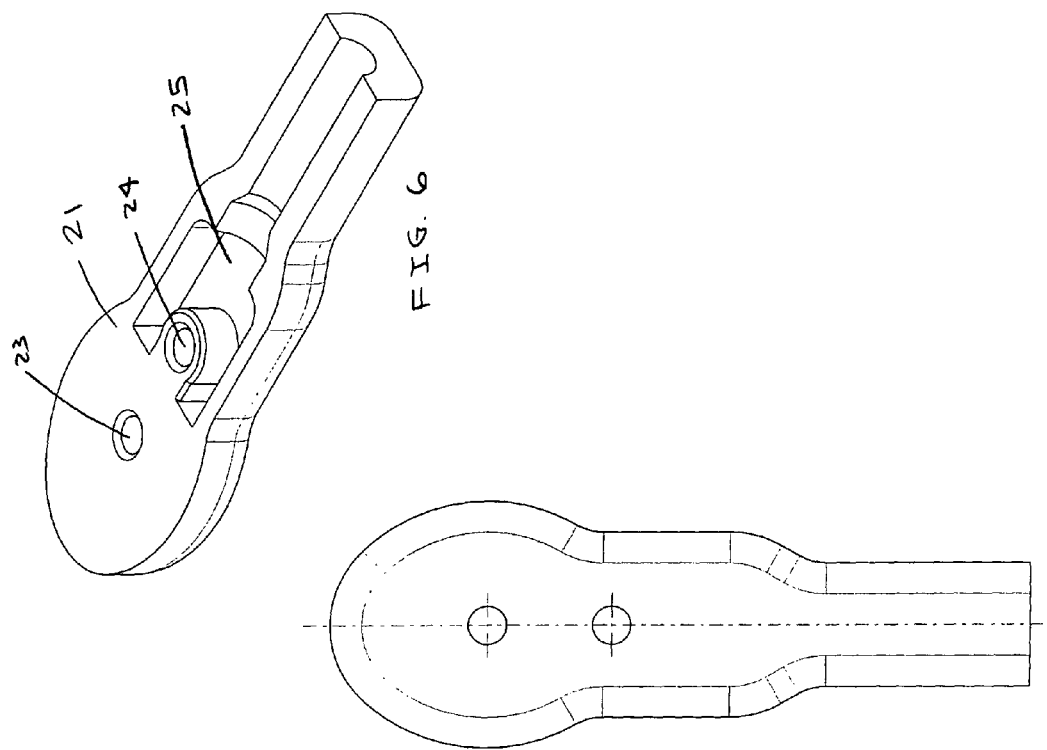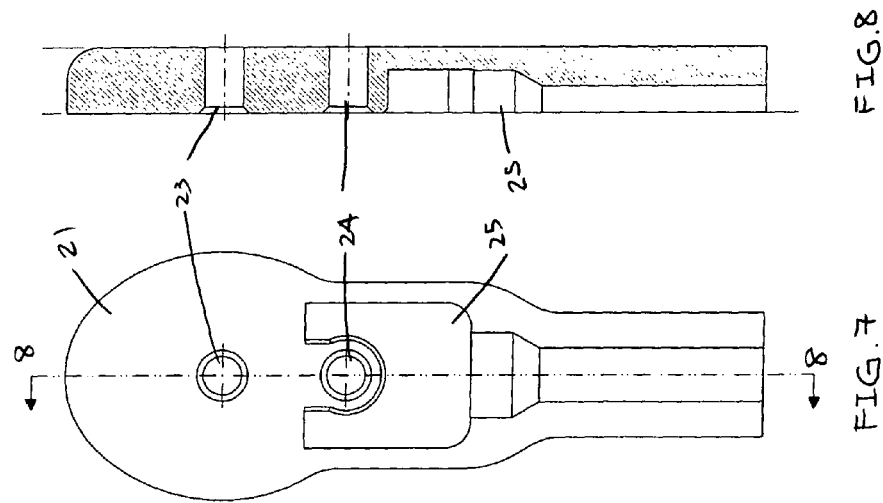

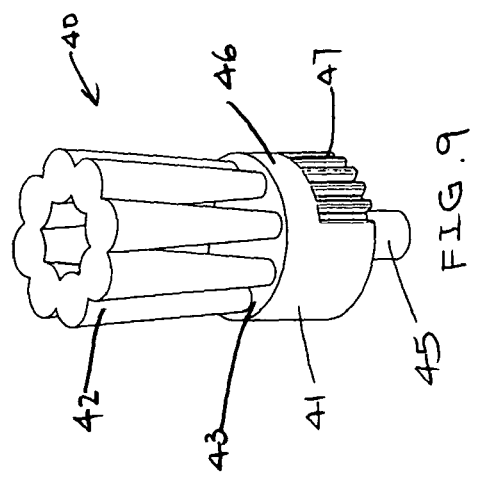
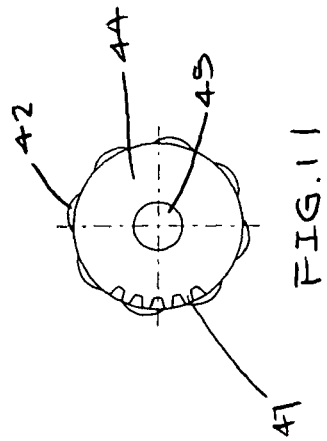
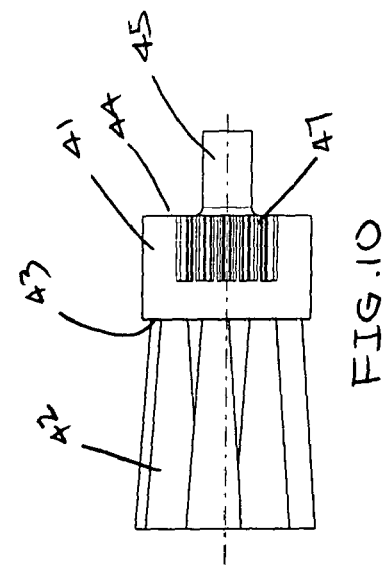
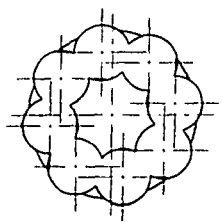

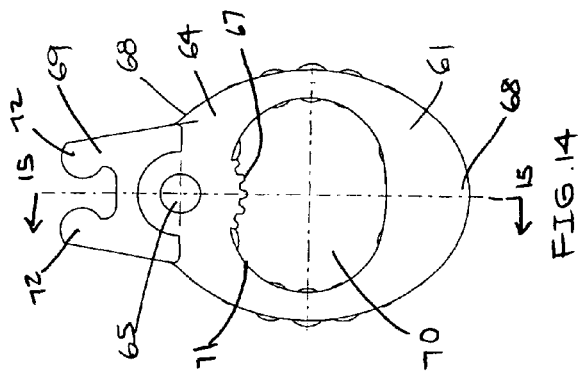
FIG. 14
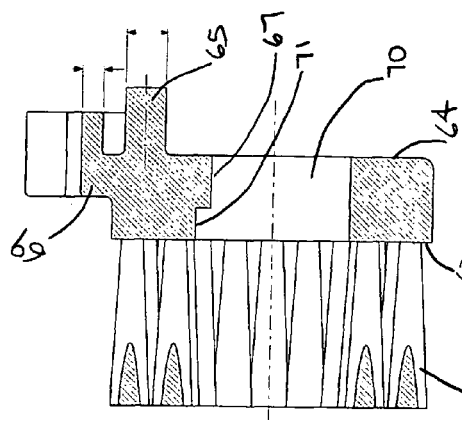
FIG. 15
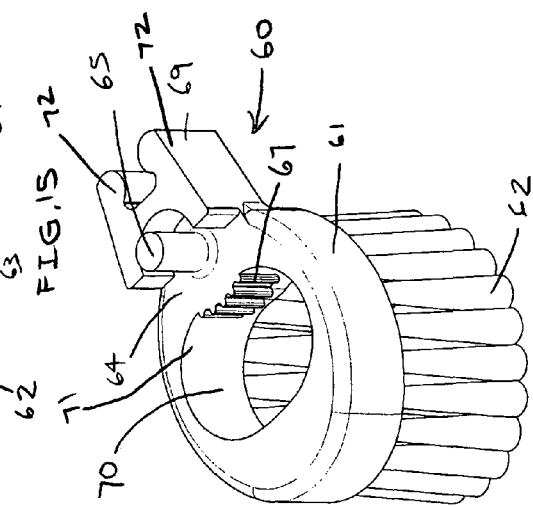
FIG. 13
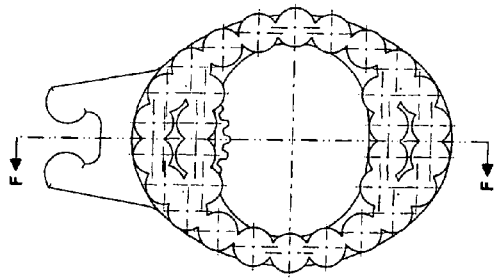
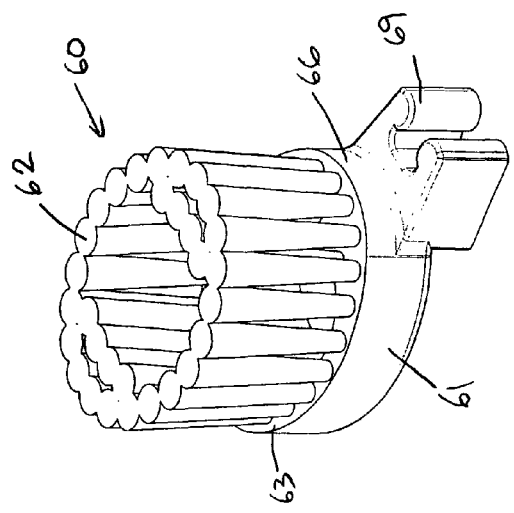
FIG. 12

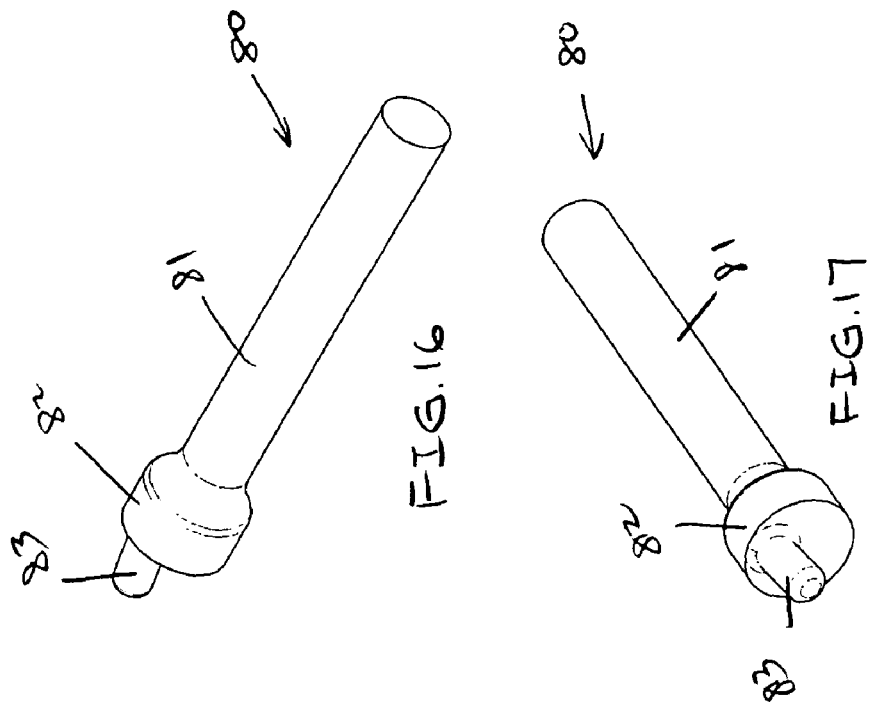
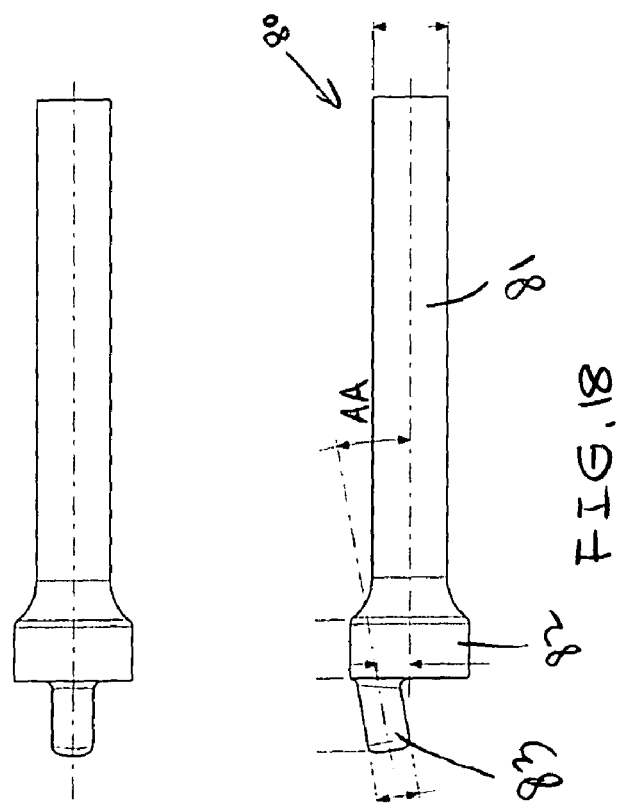

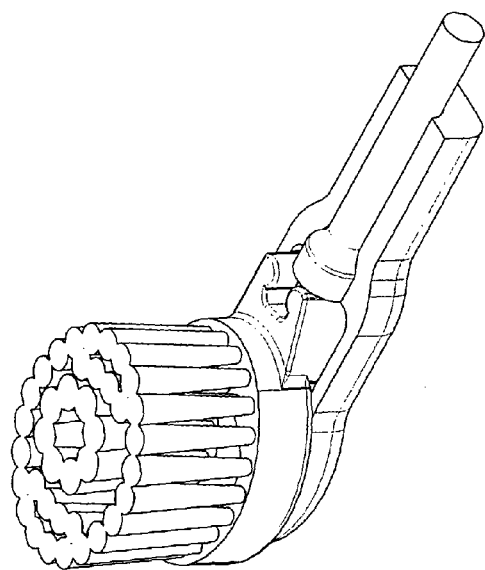
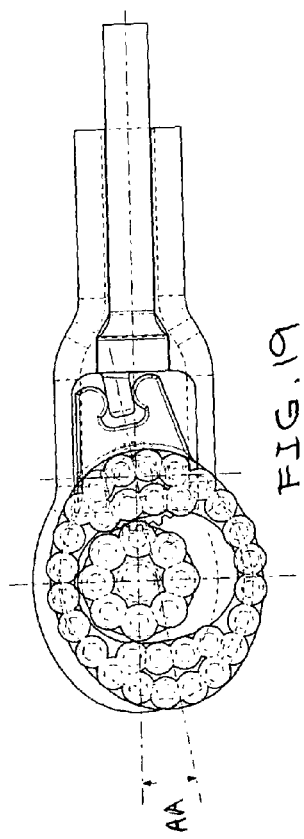
FIG. 19
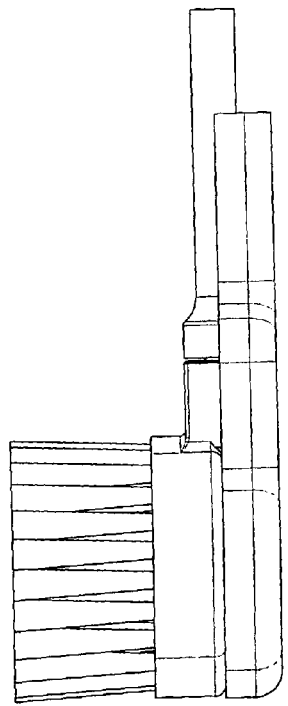
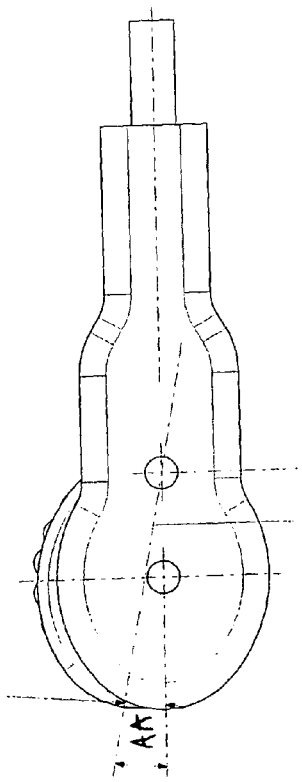
FIG. 20

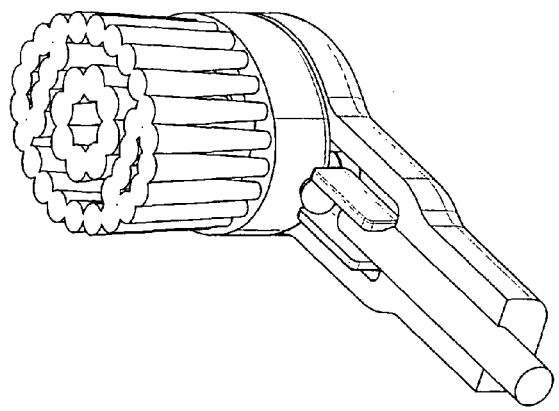
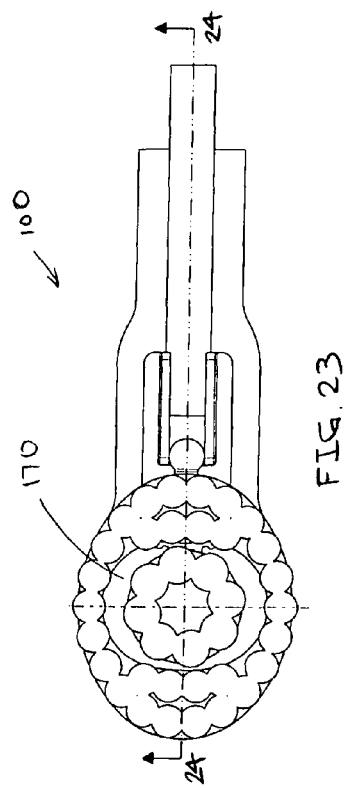
FIG. 23
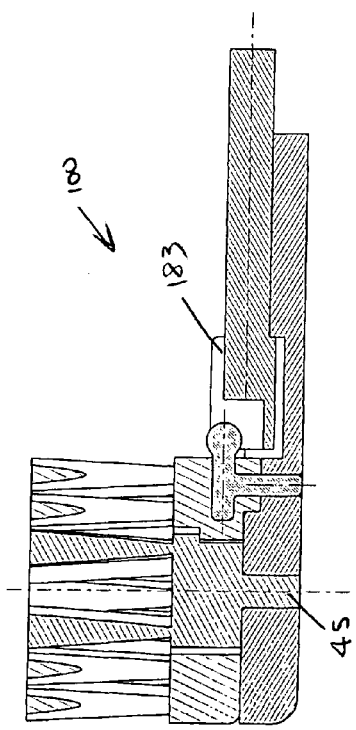
FIG. 24
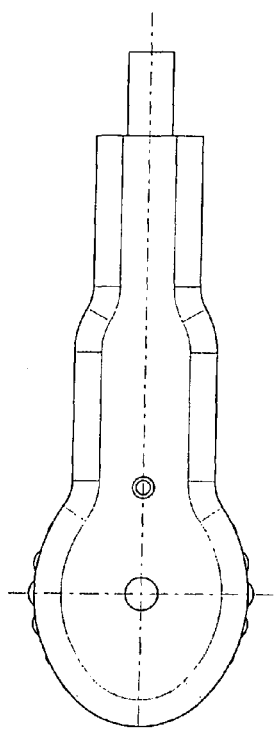

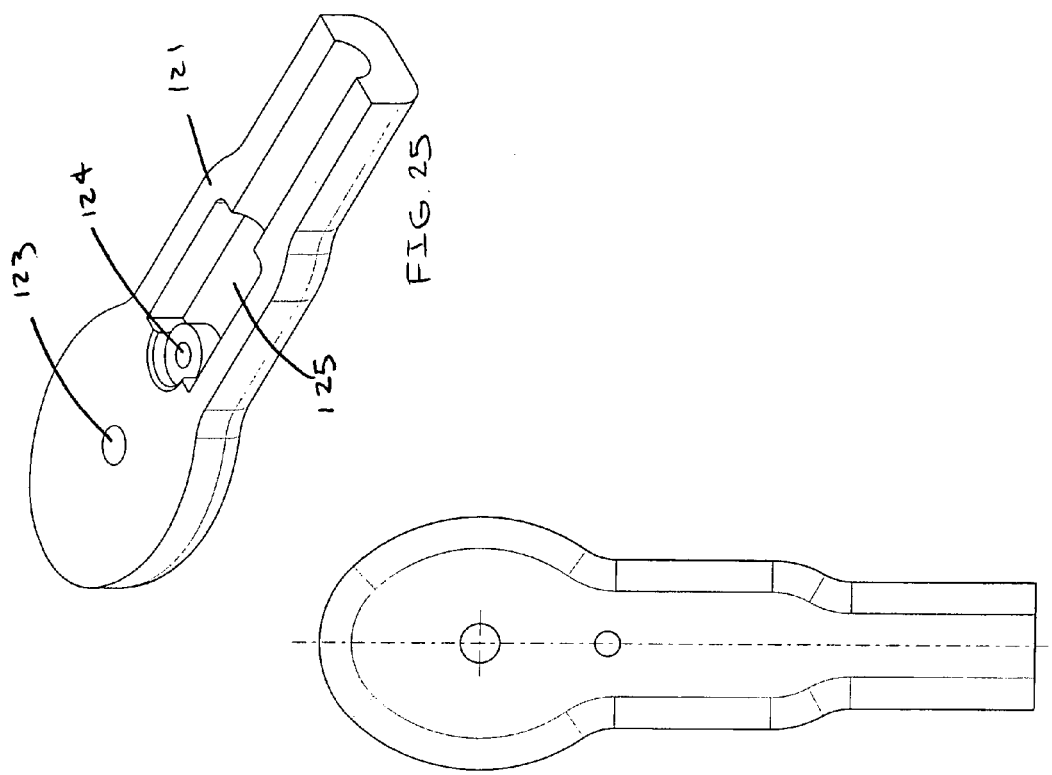
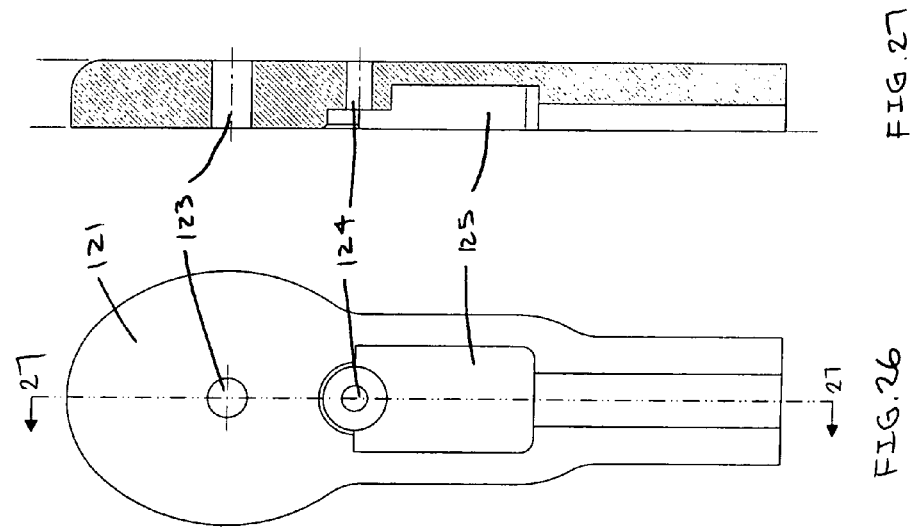
FIG. 25
FIG. 26
FIG. 27

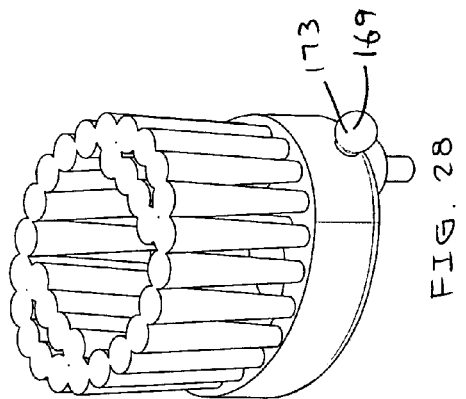
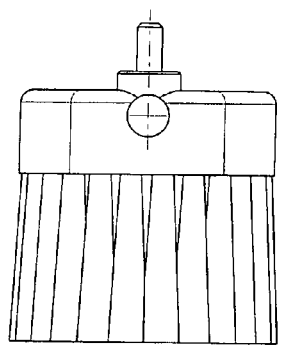
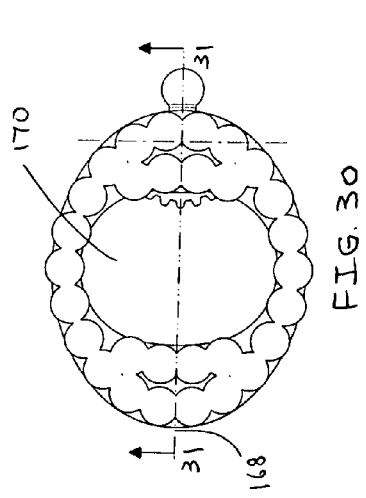
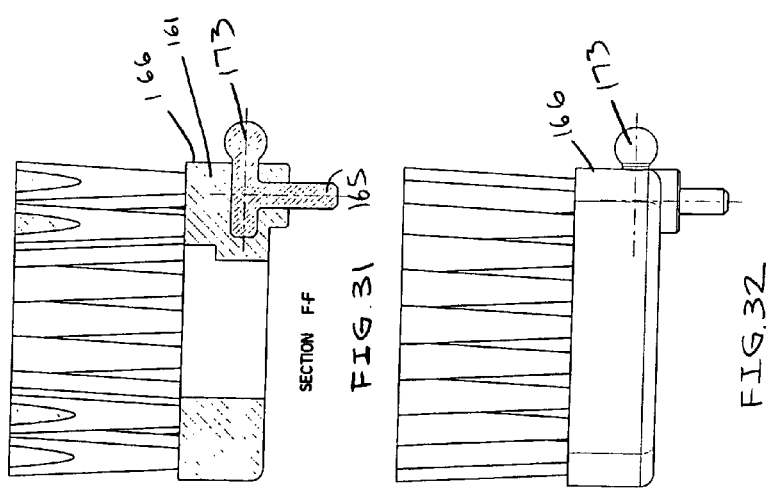

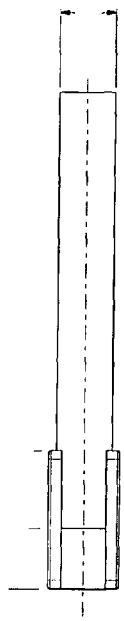
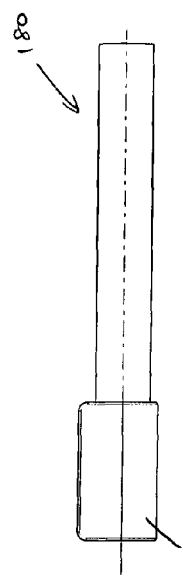
FIG. 35
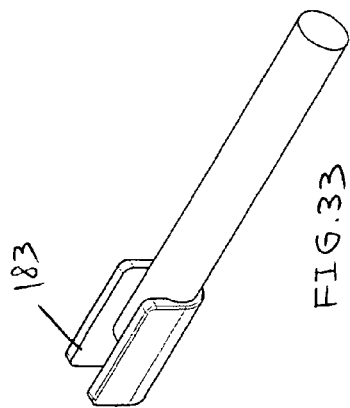
FIG. 33
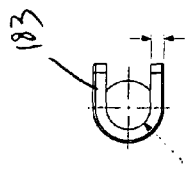
FIG. 36
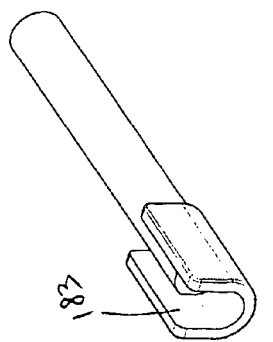
FIG. 34

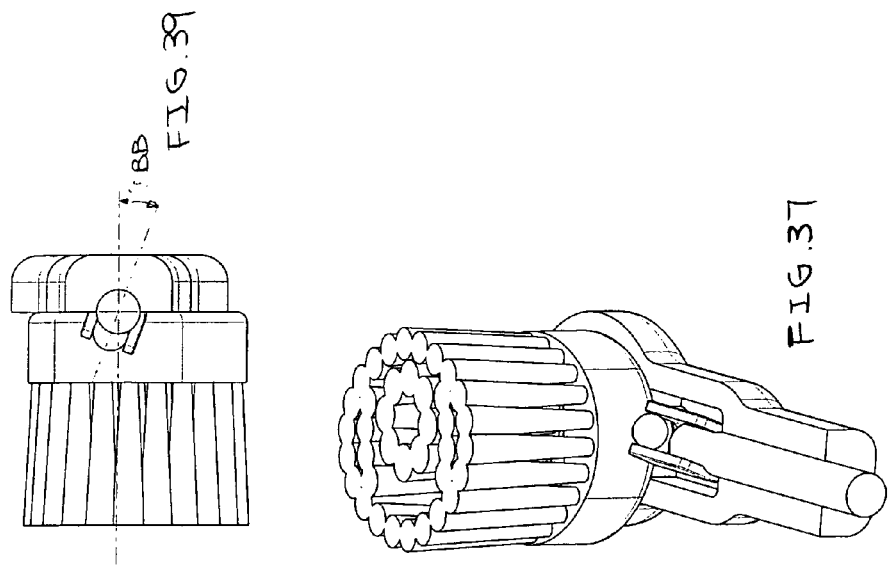
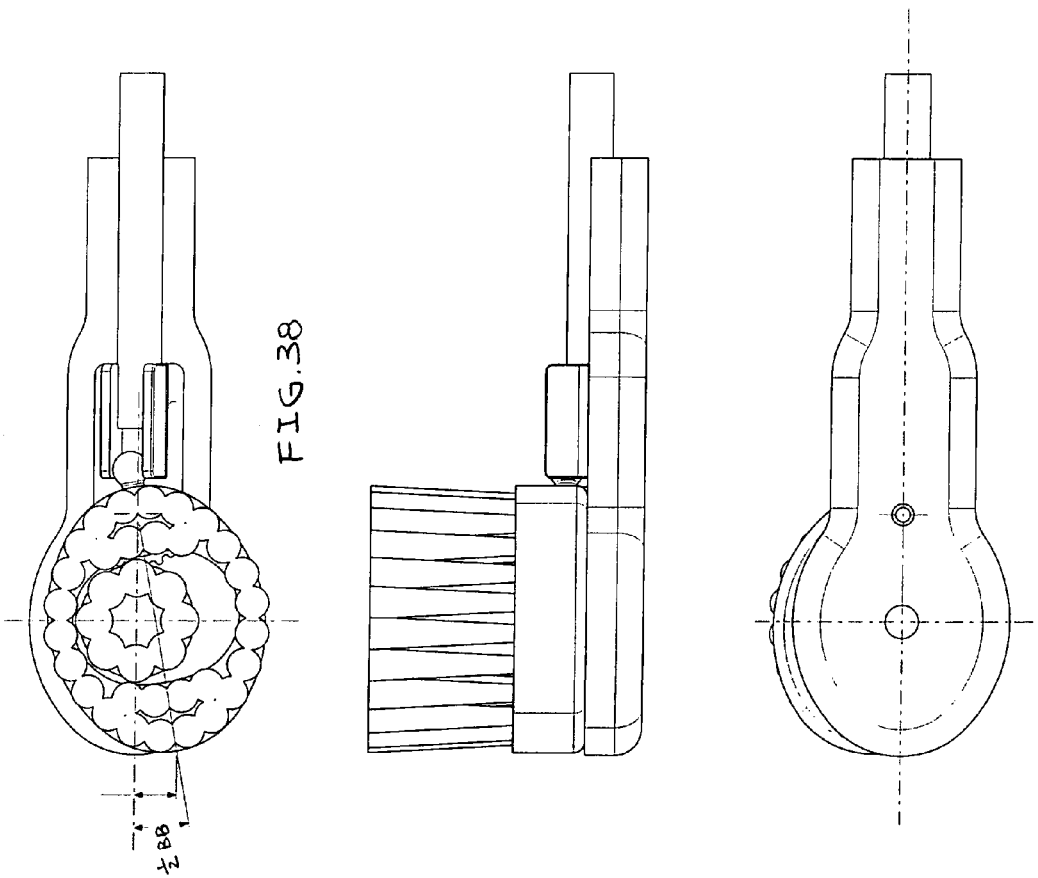

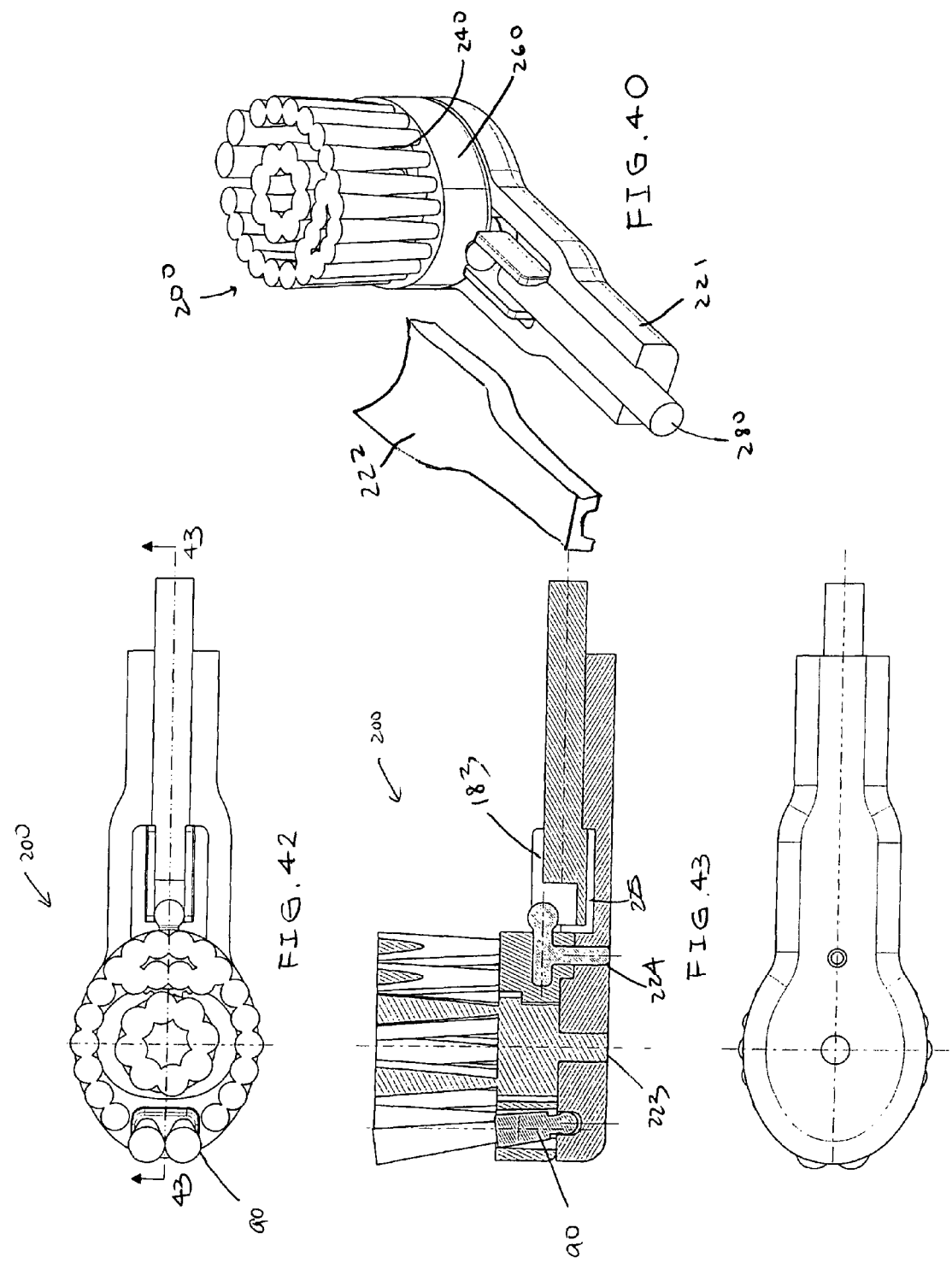

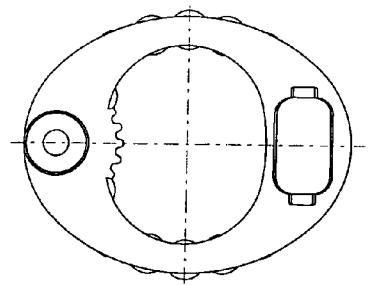
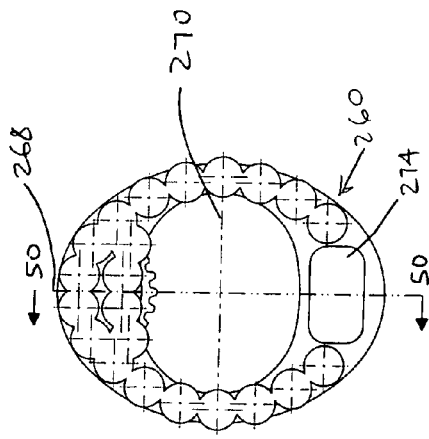
FIG. 50
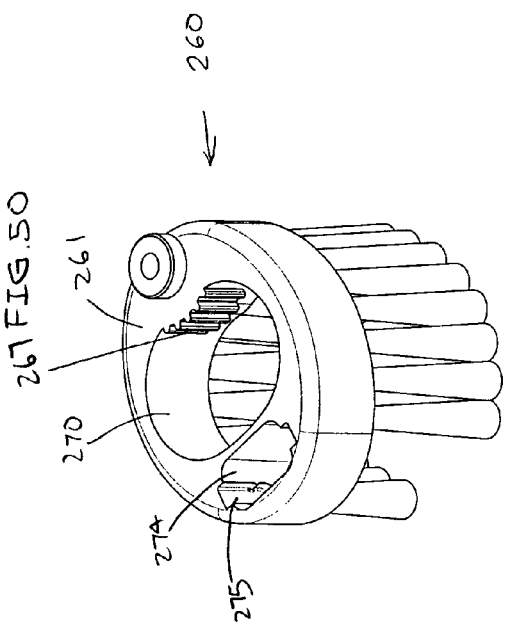
FIG. 48
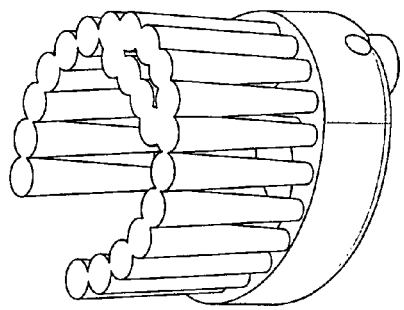
FIG. 47
FIG. 49

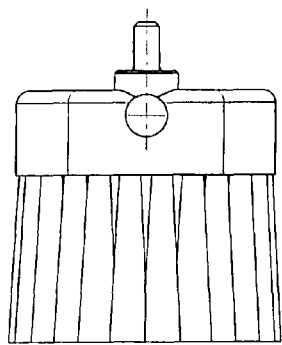
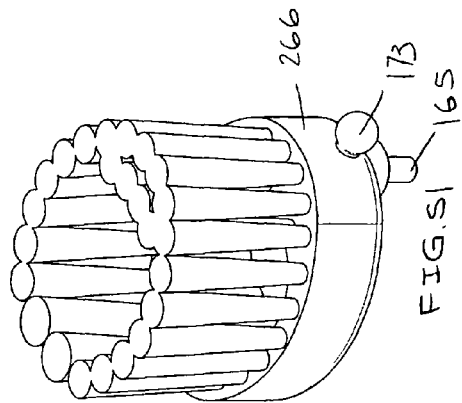
FIG.51
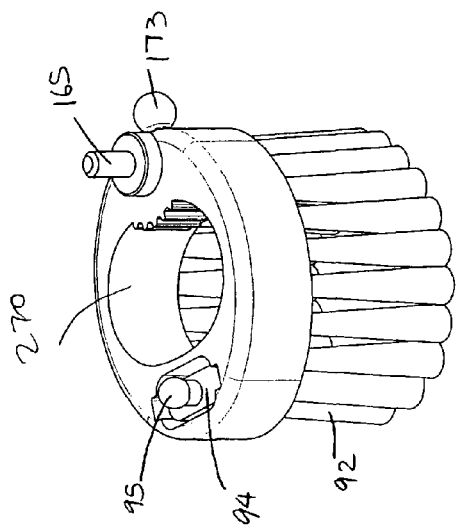
FIG.52
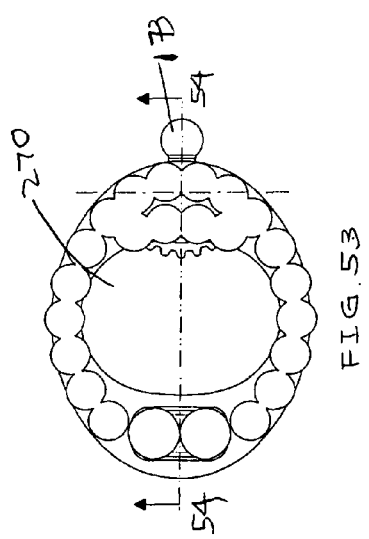
FIG.53
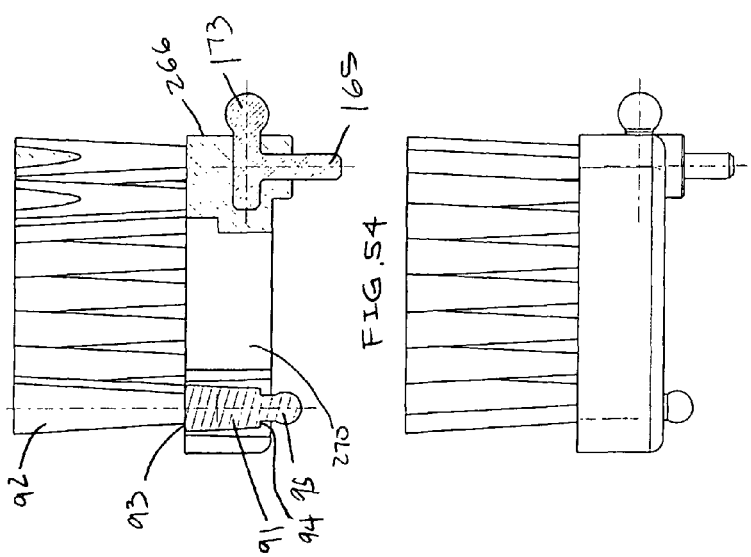
FIG.54

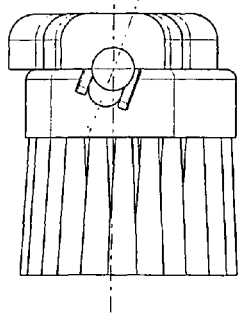
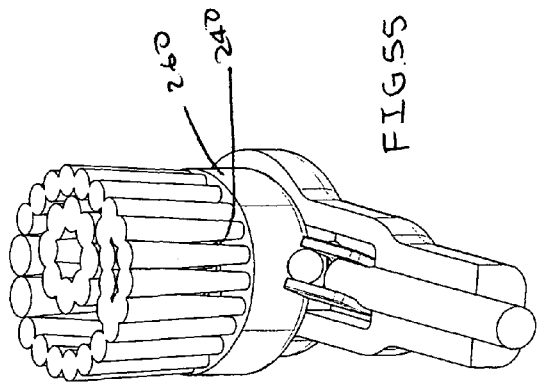
FIG. 57
FIG. 55
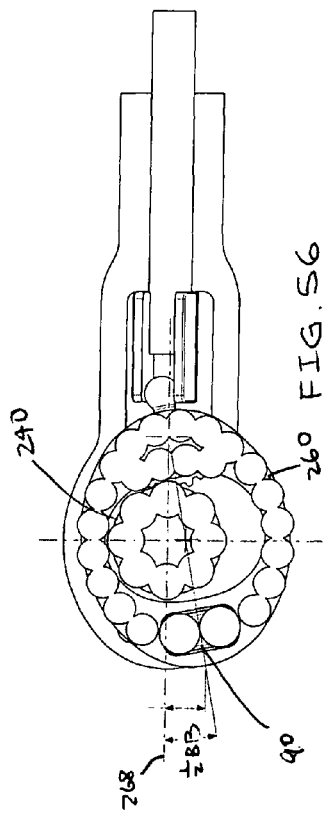
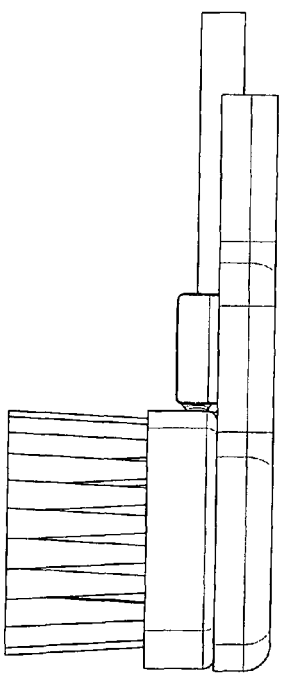
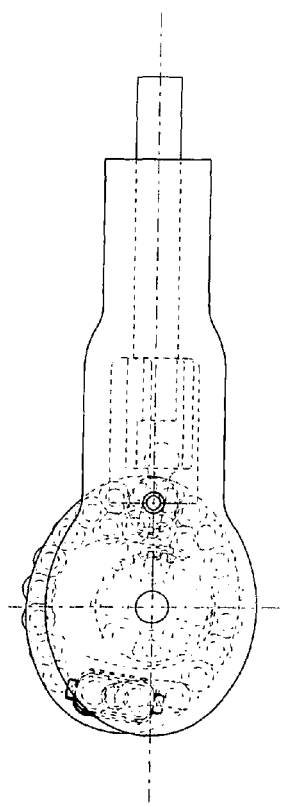
FIG. 56

MOTORIZED TOOTHBRUSH TIP HAVING INNER AND OTHER HEADS COUNTER AROUND DIFFERENT AXES

FIELD OF THE INVENTION

The invention relates to powered toothbrushes. In particular, the invention relates to a brush tip for a powered toothbrush having two nesting brush heads that counter-rotate around different axes.

BACKGROUND OF THE INVENTION

In a conventional motorized toothbrush of the multi-head type, a disposable brush tip is detachably secured to the handle of the toothbrush. The tip has a plurality of brush heads, which oscillate (as by rotation) under the power of the motor. Each brush head has a plurality of tufts of bristles.

Existing motorized toothbrushes have relatively small "coverage", i.e. they do not clean large surface areas at one time. This is because the brush heads are relatively small. If they are made too large, they will put an excessive load on the motor as well as cause irritation to the soft tissue of the mouth.

Furthermore, some users operate such toothbrushes improperly. Instead of applying only light pressure, they force the bristles hard against the teeth. Under such conditions, the distal end of each tuft of bristles stays in the same place and the tufts twist themselves tightly in alternate directions. This makes the brushing less effective, because the bristles do not scrub the surfaces of the teeth.

It would be advantageous to provide a multi-head motorized toothbrush tip that would have greater coverage than conventional toothbrushes. It would be advantageous to provide a multi-head toothbrush tip whereby the cleaning member, i.e. the tufts of bristles and/or rubber-like extensions, extending from the brush heads are arranged in a pattern so as to cover a larger area than the brush head itself.

It would also be advantageous to provide a multi-head motorized toothbrush tip that would perform better even when the user applies excessive pressure against the tooth surfaces to be cleaned.

In accordance with the invention, a brush tip for a motorized toothbrush has a first brush head and a second brush head. The second brush head surrounds the first brush head, and the first and second brush heads rotate around different axes in response to motion produced by the toothbrush motor. Means are provided for counter-rotating and accelerating the first and second brush heads either at equal or different angular speeds.

Because the second brush head surrounds the first brush head, the two heads together have a relatively large area and, therefore, greater coverage. And, because the two brush heads counter-rotate at different axes, their bristles do not twist themselves together even when pressed hard against the teeth.

In preferred embodiments, the first and second brush heads are accelerated in opposite directions, the first brush head is circular, and the second brush head is elliptical. The elliptical brush head provides greater coverage than a circular brush head and the opposite motions and rotation at different axes of the heads make it impossible for the bristles attached to the first brush head to twist into the bristles attached to the second brush head. Further, the first and second brush heads may be both circular with the bristles or tufts of bristles on the brush heads being positioned in a splayed manner such that it is impossible for the bristles on the first and second brush heads to twist into each other.

For toothbrushes of the type wherein the motor produces oscillating rotational motion of a shaft, a gear is mounted at the end of the shaft and is used to rotate the brush heads. For toothbrushes of the type wherein the motor produces reciprocating linear motion of an actuator, two connecting rods are used to convert this linear motion into oscillating rotational motion of the brush heads. However, most motorized toothbrushes generally use a battery-powered DC motor as a source of mechanical energy. This mechanical energy takes the form of a one-way rotation of a shaft that is mechanically coupled to the rotor of the DC motor. Therefore, for the above-discussed mechanisms to be usable, the motorized toothbrush must include a motion conversion mechanism that converts the one-way shaft rotation produced by the DC motor into linear reciprocation or into rotational oscillation. This increases cost of manufacture, diminishes power available to the toothbrush heads, and increases noise of the toothbrush during use.

Commonly-owned U.S. Pat. No. 6,349,442 discloses different head rotation mechanisms, each designed for use with a particular type of motorized toothbrush. One mechanism is designed for use with a motorized toothbrush wherein an actuator, such as a plunger, is linearly reciprocated. The other mechanism is designed for use with a motorized toothbrush wherein a shaft is rotationally oscillated.

Commonly-owned U.S. Pat. No. 6,751,823 discloses a motorized toothbrush wherein one-way rotation of a shaft can be used as the mechanical input to drive two counter-rotating heads that rotate about a common axis to prevent the bristles from twisting together.

Other prior art toothbrush tips are disclosed in U.S. Pat. Nos. 5,416,942, 5,850,655, 5,974,613, 6,665,901, 6,957,468, 7,146,675, and 7,392,562.

The present invention discloses an improved motorized toothbrush that has two nesting brush heads that counter-rotate around different axes and driven by either a one-way rotational or oscillating rotational shaft. The two nesting brush heads may rotate and accelerate at the same or different angular speeds.

SUMMARY OF THE INVENTION

The toothbrush tip of the present invention has two geared, counter-rotating, brush heads that rotate around separate axes of rotation and are independently axially mounted. The second and outer brush head surrounds the first and inner brush head to create a toothbrush tip having four different motions/directions. In another embodiment, the second and outer brush head also surrounds and supports a third tilting/rocking brush head to create a toothbrush tip having six different motions/directions. Each of the first, second and third brush head has a plurality of cleaning members, such as bristles, tufts of bristles and/or rubber-like extensions mounted thereon.

In accordance with the present invention, first and second brush heads are provided such that the second brush head surrounds the first brush head. The first and second brush heads have different axes of rotation. The toothbrush motor drives an acceleration mechanism that provides counter-rotation of the first and second brush heads at equal or unequal angular acceleration.

The brush tip of the present invention comprises a housing, first and second brush heads, means for counter rotating and accelerating the first and second brush heads, and a shaft.

The housing supports and holds the first and second brush heads and has first and second openings that correspond, respectively, to the axes of rotation of the first and second brush heads. An optional cover matingly engages the housing to enclose the shaft.

The first brush head has a generally cylindrical body, with a first set of cleaning members (i.e. bristles) extending from one planar surface. On the opposite planar surface is a centrally and axially extending pin for engaging the first opening of the housing. Along a portion of the curve side wall of the cylindrical body is a plurality of elongated gear teeth having axes parallel to the central axis of the body.

The second brush head has a generally elliptic cylindrical body, and having a generally central and elliptical aperture where the first brush head nests therein. A second set of cleaning members (i.e. bristles) extending from one planar surface. On the opposite planar surface, near the convex side wall and on the major semi-axis is a perpendicularly extending pin for engaging the second opening of the housing. Extending from the convex side wall of the elliptic cylindrical body along the major semi-axis is a crank engaging element for receiving the crank member of the shaft. Extending along a portion of the concave side wall of the elliptical aperture near the major semi-axis is a plurality of gear teeth having axes parallel to the central axis of the body. The gear teeth of the first and second brush heads engage each other when first brush head is nested within the second brush head.

The shaft is coupled to a motor for rotation or oscillating rotation about the shaft axis. Extending from the distal end of the shaft near the perimeter is a crank member. The crank member engages the crank engaging element of the second brush head.

Upon movement of the shaft, the crank element drives the second brush head to oscillate about its own axis of rotation, and through the gear teeth, causes the first brush head to oscillate in the opposite direction about its own axis of rotation within the elliptical aperture of the second brush head. The gear teeth of the first and second brush heads are arranged to have equal or unequal pitch circle radii to achieve equal or unequal angular acceleration, respectively, of the first and second brush heads.

The cleaning members (i.e. bristles) on the first and second brush heads may have different patterns or combination of patterns such as round, partially non-round or non-round. Further, the bristles may be continuous or interrupted. The distal ends of the bristles may also be splayed to form patterns (e.g. elliptical) different from the footprints of the bristles (e.g. round).

BRIEF DESCRIPTION OF THE DRAWINGS

Preferred embodiments of the present invention have been chosen for purposes of illustration and description and are shown in the accompanying drawings forming a part of the specification wherein:

FIG. 1 is a perspective view of the motorized toothbrush tip of the present invention with the optional cover removed and for use with a one-way rotational shaft.

FIG. 2 is the top plan view of FIG. 1.
FIG. 3 is a bottom plan view of FIG. 1.
FIG. 4 is a cross-sectional view taken along line 4-4 of FIG. 2.
FIG. 6 is a perspective view of the housing.
FIG. 7 is a top plan view of FIG. 6.
FIG. 8 is a cross-sectional view taken along line 8-8 of FIG. 7.
FIG. 9 is a perspective view of the first brush head.
FIG. 10 is a side view of FIG. 9.
FIG. 11 is a bottom plan view of FIG. 9.
FIG. 12 is a top perspective view of the second brush head.
FIG. 13 is a bottom perspective view of FIG. 12.
FIG. 14 is a bottom plan view of FIG. 12.
FIG. 15 is a cross-sectional view taken along line 15-15 of FIG. 14.
FIG. 16 is a top perspective view of the shaft.
FIG. 17 is an opposite perspective view of FIG. 16.
FIG. 18 is a side view of FIG. 16.
FIG. 19 is a top plan view of the motorized toothbrush tip of FIG. 1 in the first extreme position while in operation.
FIG. 20 is a bottom plan view of FIG. 19.
FIG. 23 is a top plan view of FIG. 21.
FIG. 24 is a cross-sectional view taken along line 24-24 of FIG. 23.
FIG. 25 is a perspective view of the housing.
FIG. 26 is a top plan view of FIG. 25.
FIG. 27 is a cross-sectional view taken along line 27-27 of FIG. 26.
FIG. 28 is a top perspective view of the second brush head.
FIG. 29 is a bottom perspective view of FIG. 28.
FIG. 30 is a top plan view of FIG. 28.
FIG. 31 is a cross-sectional view taken along line 31-31 of FIG. 30.
FIG. 32 is a side view of FIG. 28.
FIG. 33 is a top perspective view of the shaft.
FIG. 34 is an opposite perspective view of FIG. 33.
FIG. 35 is a side view of FIG. 33.
FIG. 36 is a front view of FIG. 33.
FIG. 37 is a perspective view the motorized toothbrush tip of FIG. 21 in the first extreme position while in operation.
FIG. 38 is a top plan view of FIG. 37.
FIG. 39 is a rear view of FIG. 37.
FIG. 40 is a perspective view of another embodiment of the present invention with a third brush head and with the optional cover removed and for use with an oscillating rotational shaft.
FIG. 42 is a top plan view of FIG. 40.
FIG. 43 is a cross-sectional view taken along line 43-43 of FIG. 42.
FIG. 47 is a top perspective view of the second brush head.
FIG. 48 is a bottom perspective view of FIG. 47.
FIG. 49 is a top plan view of FIG. 47.
FIG. 50 is a cross-sectional view taken along line 50-50 of FIG. 49.
FIG. 51 is a top perspective view of second and third brush heads.
FIG. 52 is the bottom perspective view of FIG. 51.
FIG. 53 is a top plan view of FIG. 51.
FIG. 54 is a cross-sectional view taken along line 54-54 of FIG. 53.
FIG. 55 is a perspective view the motorized toothbrush tip of FIG. 40 in the first extreme position while in operation.
FIG. 56 is a top plan view of FIG. 55.
FIG. 57 is a rear view of FIG. 55.

DETAILED DESCRIPTION OF PREFERRED EMBODIMENTS

Figure 5:
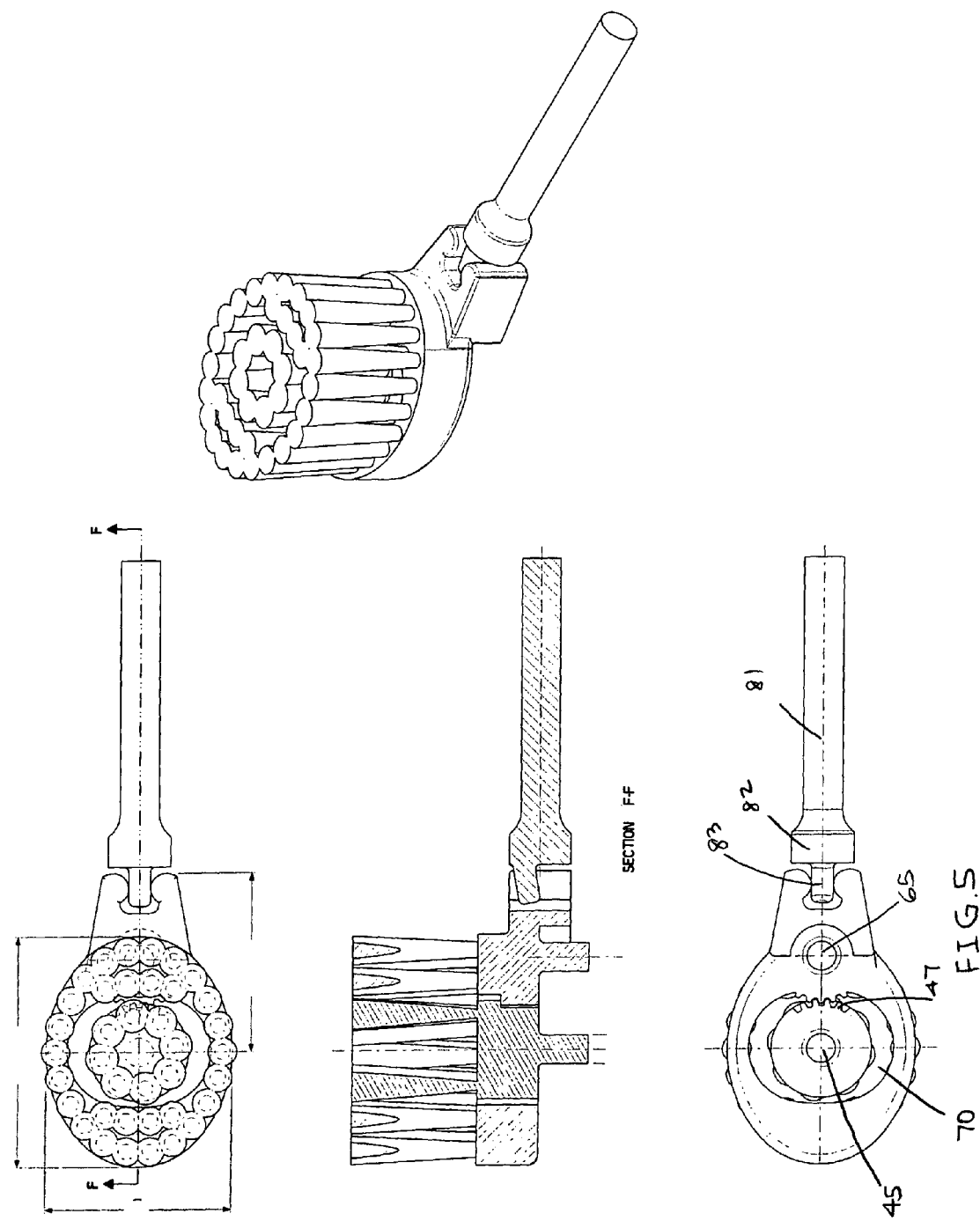
FIG. 5 is a bottom view similar to FIG. 3, with the housing removed.

With reference to the drawings wherein the same reference number illustrates the same element throughout, FIGS. 1-5 show a motorized toothbrush tip 10 of the present invention, which includes a housing 21, a first brush head 40, a second brush head 60 and a shaft 80.

As shown in FIGS. 1-5, the housing 21 has an optional cover 22. The housing 21 supports and holds the first brush head 40 and the second brush head 60. The cover 22 mates with the housing 21 to enclose the shaft 80.

As shown in detail in FIGS. 6-8, housing 21 has first opening 23 and second opening 24 that correspond, respectively, to the axes of rotation of the first brush head 40 and the second brush head 60. Housing 21 also has a cavity 25 that accommodates the shaft 80 and the crank engaging element 69 of the second brush head 60 (to be described below). The housing 21 preferably has a shape that corresponds to the second brush head 60.

As shown in detail in FIGS. 9-11, the first brush head 40 has a generally cylindrical body 41. A first set of bristles 42 extend from one planar surface 43 of the body 41. On the opposite planar surface 44 of body 41 is a centrally and axially extending pin 45 that engages the first opening 23 of housing 21. When pin 45 is placed into first opening 23 of housing 21, any known means of securing the pin 45 to the housing 21 while allowing pin 45 to freely rotate can be used. For example, pin 45 may have an enlarged head at its distal end to prevent it from disengaging from the housing 21. Along a portion of the curve side wall 46 of the body 41 is a plurality of elongated gear teeth 47 having axes parallel to the central axis of the cylindrical body 41.

As shown in detail in FIGS. 12-15, the second brush head 60 has a generally elliptic cylindrical body 61 with a generally central and elliptical aperture 70 where the first brush head 40 nests therein. A second set of bristles 62 extend from one planar surface 63 of the body 61. On the opposite planar surface 64 of body 61, near the convex side wall 66 and on the major semi-axis 68 (which is line 15-15 of FIG. 14) is a perpendicularly extending pin 65. When pin 65 is placed into second opening 24 of housing 21, any known means of securing the pin 65 to the housing 21 while allowing pin 65 to freely rotate can be used. For example, pin 65 may have an enlarged head at its distal end to prevent it from disengaging from the housing 21. Extending from the convex side wall 66 of the elliptic cylindrical body 61 along the major semi-axis 68, adjacent the opposite planar surface 64 is a crank engaging element 69 having a pair of arms 72 for receiving and engaging the crank member 83 of the shaft 80. Extending along a portion of the concave side wall 71 of the aperture 70 near the major semi-axis 68 is a plurality of elongated gear teeth 67 having axes parallel to the central axis of the elliptic cylindrical body 61.

As shown in detail in FIGS. 16-18, the shaft 80 has an elongated body 81. One end of the shaft 80 is coupled to a toothbrush motor (not shown) for rotation about the shaft axis. At the distal end of the body 81 is an enlarged head 82 with a crank member 83. The central axis of the crank member 83 and the central axis of the body 81 are displaced at an acute angle AA, with the distal end of the crank member 83 directed towards, but not intersecting with the central axis of the body 81.

With the first brush head 40 nesting within the aperture 70 of the second brush head 60, the corresponding gear teeth 47 and 67 of the first and second brush heads 40 and 60 engage each other. Upon rotational movement of the shaft 80, the crank element 83 causes the arms 72 of the crank engaging element 69 of the second brush head 60 to oscillate about its own axis of rotation, and the gear teeth 67 interact with the gear teeth 47 to cause the first brush head 40 to oscillate in the opposite direction about its own axis of rotation within the elliptical aperture 70 of the second brush head 60. The gear teeth 47 and 67 of the first and second brush heads 40 and 60 can be arranged to have equal pitch circle radii such that the first and second brush heads 40 and 60 have equal angular acceleration upon rotation of shaft 80. Alternatively, the gear teeth 47 and 67 of the first and second brush heads 40 and 60 can be arranged to have different pitch circle radii such that the first and second brush heads 40 and 60 have different angular acceleration upon rotation of shaft 80.

FIGS. 19-20 illustrate an extreme position of first and second brush heads 40 and 60 while in operation. The opposite extreme position is mirror images of FIGS. 19-20. The angle AA of the crank member 83 relative to the central axis of the body 81 is the same as the angle of displacement of the central axis of the first brush head 40 from the major semi-axis 68 of the second brush head 60.

FIGS. 21-24 show an alternate motorized toothbrush tip 100 of the present invention for use with an oscillating rotational shaft 180. The toothbrush tip 100 includes a housing 121, first brush head 140, second brush head 160, and a shaft 180. Housing 121 includes an optional cover 122. The housing 121 supports and holds the first brush head 140 and the second brush head 160. The optional cover 122 mates with the housing 121 to enclose the shaft 180.

As shown in detail in FIGS. 25-27, housing 121 is similar to housing 21 of FIGS. 6-8, and has first opening 123 and second opening 124 that correspond, respectively, to the axes of rotation of the first brush head 140 and the second brush head 160. Housing 121 also has a cavity 125 that accommodates the shaft 180 and the cam ball 173 of the second brush head 160 (to be described below). The housing 121 preferably has a shape that corresponds to the second brush head 160.

The first brush head 140 is identical to the first brush head 40 shown in FIG. 9-11. The centrally and axially extending pin 45 engages the first opening 123 of housing 121. When pin 45 is placed into first opening 123 of housing 121, any known means of securing the pin 45 to the housing 121 while allowing pin 45 to freely rotate can be used. For example, pin 45 may have an enlarged head at its distal end to prevent it from disengaging from the housing 121.

As shown in detail in FIGS. 28-32, the second brush head 160 is similar to the second brush head 60 shown in FIGS. 12-15, with a different crank engaging element. Instead of a pair of arms 72 of crank engaging element 69, a cam ball 173 extends from the convex side wall 166 of the elliptic cylindrical body 161 along the major semi-axis 168 (which is line 31-31 of FIG. 30) adjacent the opposite planar surface 164. Cam ball 173 engages the crank member 183 of shaft 180. FIG. 31 shows the cam ball 173 to be a unitary component with pin 165, preferably made from a metal, and embedded in body 161. However, cam ball 173 and pin 165 can be integral to the body 161 from the same material.

As shown in detail in FIGS. 33-36, the shaft 180 has an elongated body 181. One end of the shaft 180 is coupled to a toothbrush motor (not shown) for oscillating rotation about the shaft axis. At the distal end of the body 181 is U-shape crank member 183 having a channel for receiving the cam ball 173.

With the first brush head 140 nesting within the aperture 170 of the second brush head 160, the corresponding gear teeth 47 and 167 of the first and second brush heads 140 and 160 engage each other. Upon oscillating movement of the shaft 180, the U-shape crank member 183 causes the cam ball 173 of the second brush head 160 to oscillate about its own axis of rotation, and the gear teeth 167 interact with the gear teeth 47 to cause the first brush head 140 to oscillate in the opposite direction about its own axis of rotation within the elliptical aperture 170 of the second brush head 160. The gear teeth 47 and 167 of the first and second brush heads 140 and 160 can be arranged to have equal pitch circle radii such that the first and second brush heads 140 and 160 have equal angular acceleration upon oscillating rotation of shaft 180. Alternatively, the gear teeth 47 and 167 of the first and second brush heads 140 and 160 are arranged to have different pitch circle radii such that the first and second brush heads 140 and 160 have different angular acceleration upon oscillating rotation of shaft 180.

FIGS. 37-39 illustrate the positions of first and second brush heads 140 and 160 with the shaft 280 in one extreme position while in operation. The opposite extreme position is mirror images of FIGS. 37-39. If the angle of oscillatory rotation of the shaft 180 is BB, then the angle of displacement of the central axis of the first brush head 140 from the major semi-axis 168 of the second brush head 160 is about half of BB (½BB).

FIGS. 40-43 show an alternate motorized toothbrush tip 200 of the present invention similar to toothbrush tip 100 of FIGS. 21-24, with an additional third brush head 90. The toothbrush tip 200 includes a housing 221, first brush head 240, second brush head 260, and a shaft 280. Housing 221 includes optional cover 222. The housing 221 supports and holds the first brush head 240 and the second brush head 260. The cover 222 mates with the housing 221 to enclose the shaft 80.

Figures 44, 45, 46:
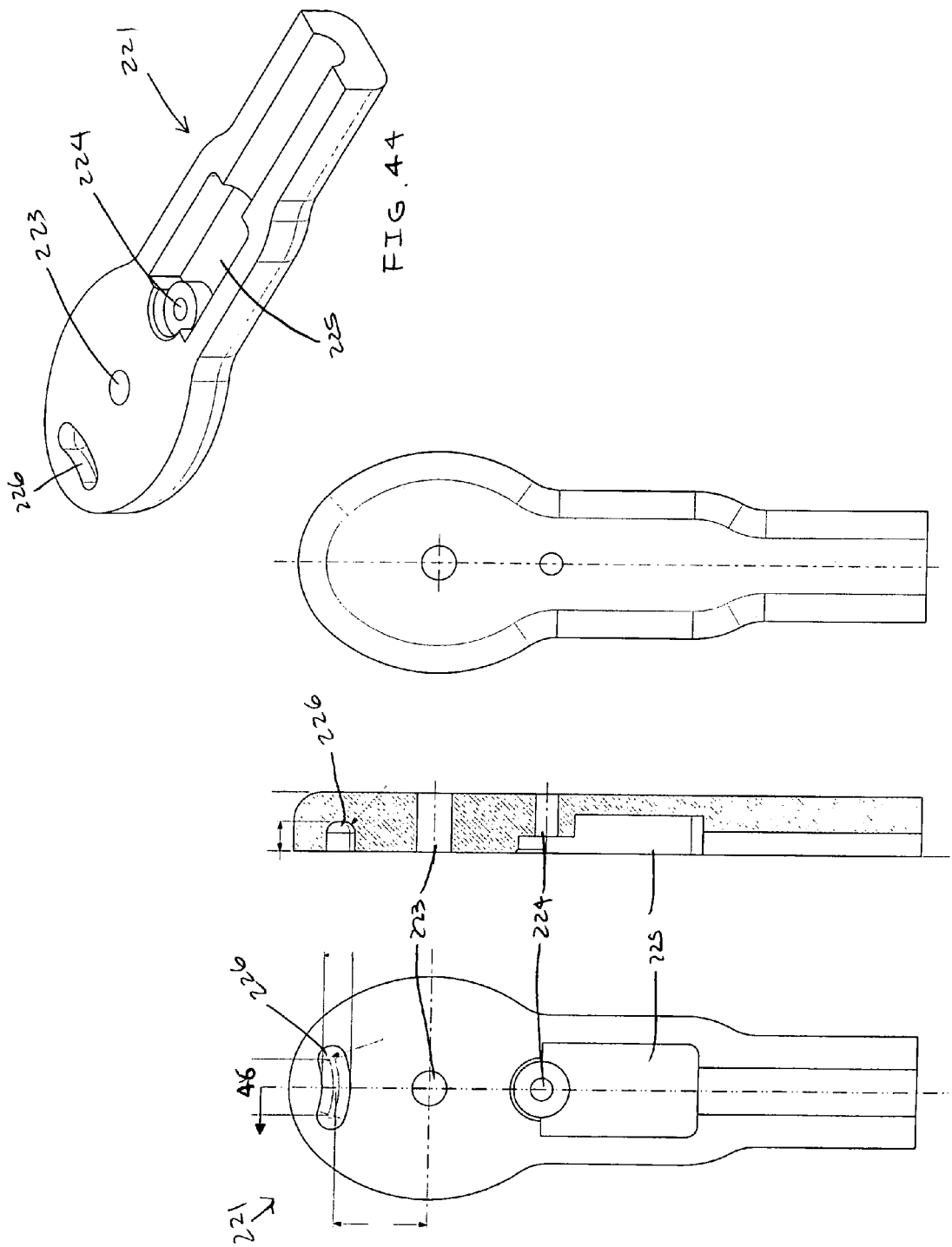
FIG. 44 is a perspective view of the housing.
FIG. 45 is a top plan view of FIG. 44.
FIG. 46 is a cross-sectional view taken along line 46-46 of FIG. 45.

As shown in detail in FIGS. 44-46, housing 221 is similar to housing 121 of FIGS. 25-27, and has first opening 223 and second opening 224 that correspond, respectively, to the axes of rotation of the first brush head 240 and the second brush head 260. Housing 221 also has a cavity 225 that accommodates the shaft 280 and the cam ball 173 of the second brush head 260 (to be described below). The housing 221 preferably has a shape that corresponds to the second brush head 260. Housing 221 also has a curve groove 226 that is in alignment with first and second openings 223 and 224 for receiving and engaging the third brush head 90.

The first brush head 240 is identical to the first brush head 40 shown in FIGS. 9-11. The centrally and axially extending pin 45 engages the first opening 223 of housing 221. When pin 45 is placed into first opening 223 of housing 221, any known means of securing the pin 45 to the housing 221 while allowing pin 45 to freely rotate can be used. For example, pin 45 may have an enlarged head at its distal end to prevent it from disengaging from the housing 221.

As shown in detail in FIGS. 47-50, the second brush head 260 is similar to the second brush head 160 shown in FIGS. 28-32, except that the elliptic cylindrical body 261 has a generally rectangular opening 274 with a pair of channels 275 on opposite walls of the opening 274 for receiving the third brush head 90. The rectangular opening 274 is symmetrical and in alignment with the major semi-axis 268 (which is line 50-50 of FIG. 49), on the other side of the aperture 270 opposite the pin 165.

As shown in detail in FIGS. 51-54, the third brush head 90 has a generally rectangular prism shape tapered body 91 smaller in dimension than the rectangular opening 274 of the second brush head 260. A third set of bristles 92 extend from the upper surface 93 of the body 91. Extending from the lower surface 94 of the body 91 is a pin 95 with an enlarged rounded head. Pin 95 engages curve groove 226 of housing 221 while allowing pivotal movement of the third brush head 90 relative to the housing 221 and allowing sliding movement of the third brush head 90 along curve groove 226. Extending from each side wall 96 of body 91 is a protrusion 97. Protrusions 97 slidably engage channels 275 in the opening 274.

Figures 21, 22:
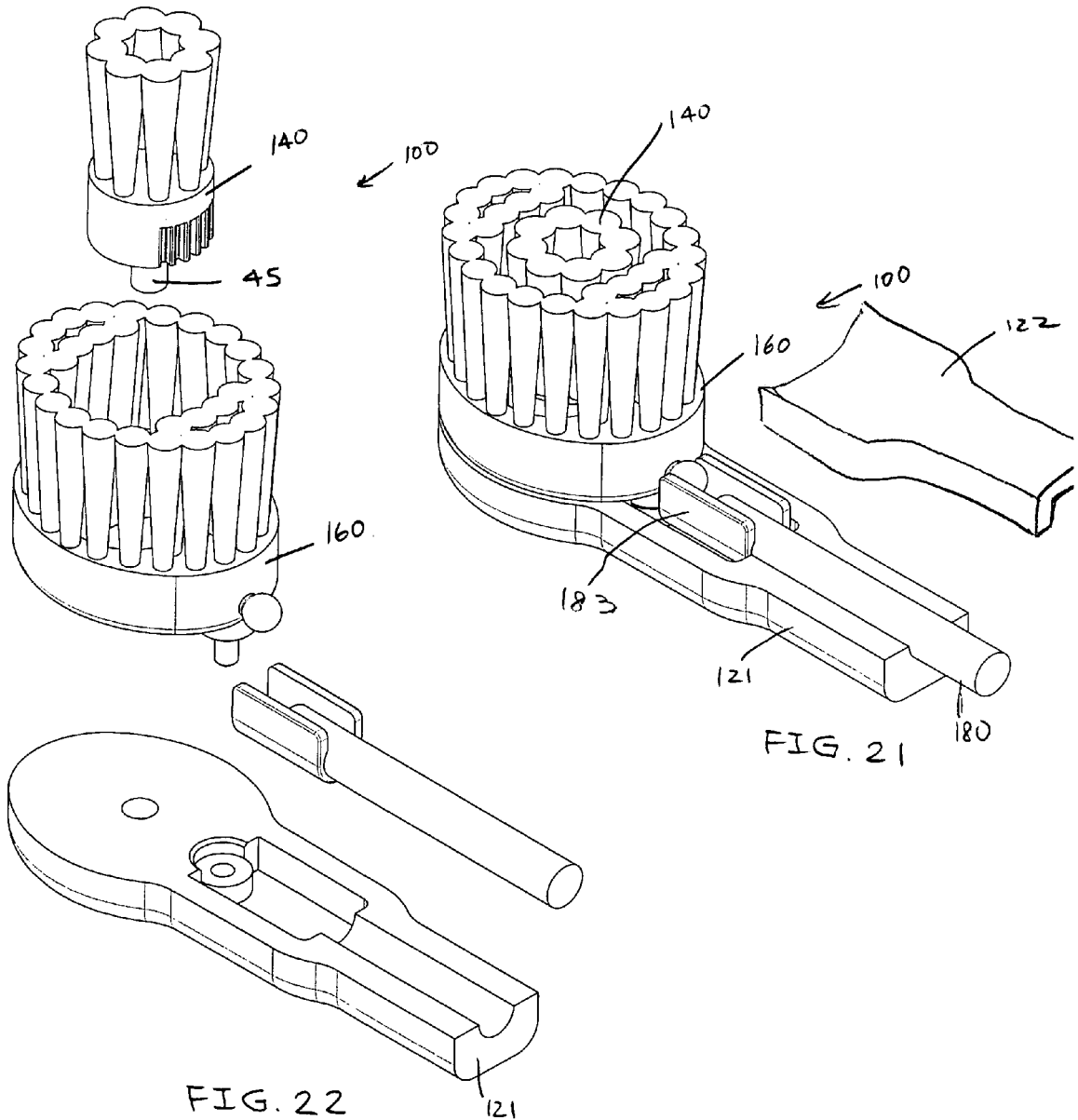
FIG. 21 is a perspective view of another embodiment of the present invention with the optional cover removed and for use with an oscillating rotational shaft.
FIG. 22 is an exploded view of the FIG. 21.
Figure 41:
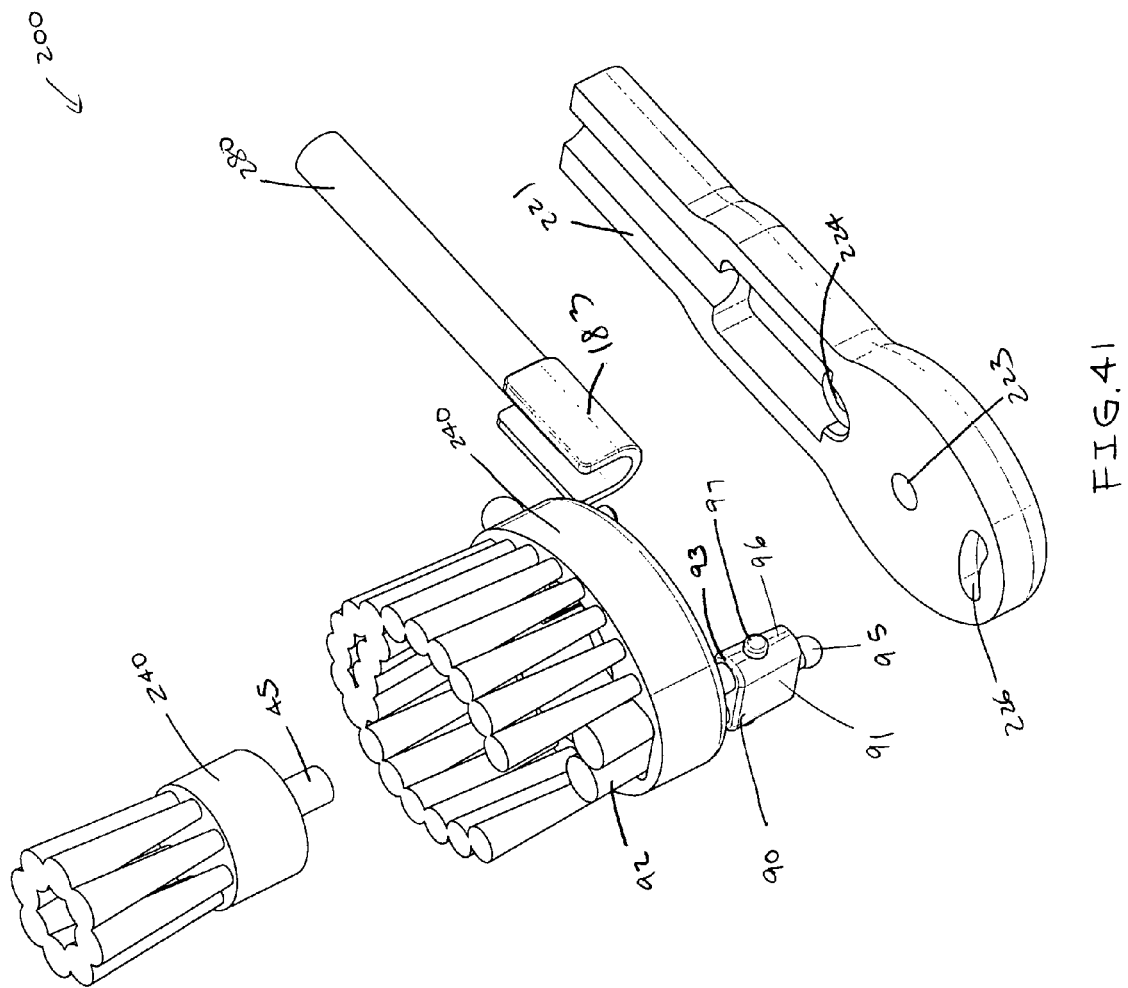
FIG. 41 is an exploded view of the FIG. 40.

The shaft 280 is identical to the shaft 180 of FIG. 21. With the first brush head 240 nesting within the aperture 270 of the second brush head 260, the corresponding gear teeth 47 and 267 of the first and second brush heads 240 and 260 engage each other. At the at rest position, as shown in FIGS. 40-43, the third set of bristles 92 of the third brush head 90 is in the center of the curve groove 226 and pivoted away from aperture 270 of the second brush head 260. Upon oscillating movement of the shaft 280, the U-shape crank member 183 causes the cam ball 173 of the second brush head 260 to oscillate about its own axis of rotation, and the gear teeth 267 interact with the gear teeth 47 to cause the first brush head 240 to oscillate in the opposite direction about its own axis of rotation within the elliptical aperture 270 of the second brush head 260. The gear teeth 47 and 267 of the first and second brush heads 240 and 260 may be arranged to have equal pitch circle radii such that the first and second brush heads 240 and 260 have equal angular acceleration upon oscillating rotation of shaft 280. While the first and second brush heads 240 and 260 oscillate in opposite direction, the third brush head 90 is guided by the rectangular opening 274 of the second brush head 260 to move back and forth along the curve groove 226 and pivot towards and away from aperture 270 of the second brush head 260. Alternatively, the gear teeth 47 and 267 of the first and second brush heads 240 and 260 may be arranged to have different pitch circle radii such that the first and second brush heads 240 and 260 have different angular acceleration upon oscillating rotation of shaft 280.

FIGS. 55-57 illustrate the positions of first, second and third brush heads 240, 260 and 90 with the shaft 280 at one extreme position while in operation. The opposite extreme position is mirror images of FIGS. 55-57 for first and second brush heads 240 and 260, with the third brush head 90 remaining at the identical position. If the angle of oscillatory rotation of the shaft 280 is BB, then the angle of displacement of the central axis of the first brush head 240 from the major semi-axis 268 of the second brush head 260 is about half of BB (½BB).

Other acceleration mechanisms know to one skilled in the art that can produce counter rotation of the first and second brush heads can be used. For example, gears, cams, wires, rotating or oscillating shaft with offset pin riding in a slot or any combination of the above can be used.

While the first brush head is shown to be cylindrical and the second brush head is shown to be elliptic cylindrical, different combination of non-circular or non-curved shapes can be used instead.

The first set of bristles on the first brush head is shown to have a circular footprint. However, different shapes footprints can be used. Similarly, the second set of bristles on the second brush head is shown to have an elliptical footprint, but other different shapes footprints can be used. Further, the first, second and third sets of bristles are shown to be formed from a plurality of tufts, but continuous bristles or rubber-like extensions can also be used, whether in combination or alone. Still further, while the first, second and third sets of bristles are shown to extend vertically from the first, second and third brush heads respectively (such that the footprint and the pattern formed from the distal ends of the bristles are the same), the bristles may also extend from the first, second and third brush heads at an angle (i.e. splayed) such that the distal ends of the bristles form a different pattern than its footprint (e.g.

circular footprint with the distal ends of the bristles forming an elliptical pattern). The distal ends of the bristles can form different patterns such as square, diamond, or other non-circular or non-linear patterns.

The features of the invention illustrated and described herein are the preferred embodiments. Therefore, it is understood that the appended claims are intended to cover the variations disclosed and unforeseeable embodiments with insubstantial differences that are within the spirit of the claims.

What we claim is:

1. A brush tip for a motorized toothbrush, comprising:
   a housing having a first opening defining a first axis of rotation, a second opening defining a second axis of rotation different from said first axis of rotation, and a cavity;
   a first brush head supported by said housing in said first opening for rotation about said first axis of rotation;
   a second brush head supported by said housing in said second opening for rotation about said second axis of rotation, said second brush head encircling said first brush head;
   means for counter rotating said first and second brush heads around said first and second axes of rotation, respectively; and
   an elongated shaft supported by said housing in said cavity for rotation about a shaft axis, engaging said second brush head to drive said first and second brush heads.

2. The brush tip of claim 1 wherein said first brush head comprises a generally cylindrical body.

3. The brush tip of claim 2 wherein said generally cylindrical body having first and second planar surfaces, a first set of cleaning members extending from said first planar surface, and a centrally and axially extending pin extending from said second planar surface for inserting into said first opening of said housing.

4. The brush tip of claim 3 wherein said generally cylindrical body further having a curve side wall, and along a portion of said curve side wall is a plurality of elongated gear teeth having axes parallel to the central axis of said cylindrical body.

5. The brush tip of claim 2 wherein said generally cylindrical body further having a curve side wall and said second brush head comprises a generally elliptic cylindrical body having a generally central and elliptical aperture where said first brush head nests therein and said elliptical aperture having a concave side wall, said counter rotating means comprises:
   a first set of gear teeth along a portion of said curve side wall of said cylindrical body having axes parallel to the central axis of said cylindrical body; and
   a second set of gear teeth along a portion of said concave side wall of said elliptic cylindrical body having axes parallel to the central axis of said elliptic cylindrical body;
   wherein said first and second sets of gear teeth interact with each other.

6. The brush tip of claim 1 wherein said second brush head comprises a generally elliptic cylindrical body having a generally central and elliptical aperture where said first brush head nests therein.

7. The brush tip of claim 6 wherein said generally elliptic cylindrical body having first and second planar surfaces and a convex side wall, a second set of cleaning members extending from said first planar surface, and a perpendicularly pin extending from said second planar surface near said convex side wall on the major semi-axis of said elliptic cylindrical body for inserting into said second opening of said housing.

8. The brush tip of claim 7 wherein said generally elliptic cylindrical body further having a crank engaging element extending from said convex side wall along the major semi-axis of the elliptic cylindrical body for receiving said elongated shaft, and said crank engaging element being supported by said housing in said cavity.

9. The brush tip of claim 8 wherein said generally elliptic cylindrical body further having a concave side wall in said elliptical aperture, and along a portion of said concave side wall is a plurality of elongated gear teeth having axes parallel to the central axis of said elliptic cylindrical body.

10. The brush tip of claim 8 wherein said elongated shaft having a distal end with a crank member for engaging said crank engaging element of said second brush head.

11. The brush tip of claim 8 wherein said crank engaging element comprises a pair of arms.

12. The brush tip of claim 11 wherein said elongated shaft having an enlarged distal end with a crank member extending therefrom for engaging between said pair of arms of said crank engaging element, said crank member having a central axis displaced at a predetermined acute angle from the central axis of said shaft, with the distal end of said crank member directed towards, but not intersecting with the central axis of said shaft.

13. The brush tip of claim 8 wherein said crank engaging element comprises a cam ball.

14. The brush tip of claim 13 wherein said elongated shaft having a crank member at its distal end for receiving said cam ball, said crank member comprises a U-shape body having a channel for receiving said cam ball.

15. The brush tip of claim 7 wherein said cleaning member is selected from the group consisting of bristle, tuft of bristles and rubber-like extension.

16. The brush tip of claim 1 wherein said counter rotating means further comprising means for accelerating said first and second brush heads at equal angular acceleration.

17. The brush tip of claim 16 wherein said first brush head comprises a generally cylindrical body and said second brush head comprises a generally elliptic cylindrical body having a generally central and elliptical aperture where said first brush head nests therein, said generally cylindrical body further having a curve side wall and said generally elliptic cylindrical body further having a generally central and elliptical aperture where said first brush head nests therein and said elliptical aperture having a concave side wall, said counter rotating means comprises:
   a first set of gear teeth along a portion of said curve side wall of said cylindrical body having axes parallel to the central axis of said cylindrical body; and
   a second set of gear teeth along a portion of said concave side wall of said elliptic cylindrical body having axes parallel to the central axis of said elliptic cylindrical body;
   wherein said first and second sets of gear teeth having equal pitch circle radii and interact with each other.

18. The brush tip of claim 1 wherein said counter rotating means further comprising means for accelerating said first and second brush heads at different angular acceleration.

19. The brush tip of claim 18 wherein said first brush head comprises a generally cylindrical body and said second brush head comprises a generally elliptic cylindrical body having a generally central and elliptical aperture where said first brush head nests therein, said generally cylindrical body further having a curve side wall and said generally elliptic cylindrical body further having a generally central and elliptical aperture where said first brush head nests therein and said elliptical aperture having a concave side wall, said counter rotating means comprises:
- a first set of gear teeth along a portion of said curve side wall of said cylindrical body having axes parallel to the central axis of said cylindrical body; and
- a second set of gear teeth along a portion of said concave side wall of said elliptic cylindrical body having axes parallel to the central axis of said elliptic cylindrical body;
- wherein said first and second sets of gear teeth having different pitch circle radii and interact with each other.

20. The brush tip of claim 1 wherein said elongated shaft having a distal end with a crank member for engaging said second brush head.

21. The brush tip of claim 1 further comprising a first set of cleaning members extending from said first brush head, distal ends of said first set of cleaning members forming a circular pattern and a second set of cleaning members extending from said second brush head, distal ends of said second set of cleaning members forming a non-circular pattern.

22. The brush tip of claim 21 wherein said distal ends of said second set of cleaning members forming an elliptical pattern.

23. The brush tip of claim 21 wherein said first and second sets of cleaning members extending substantially vertically from said first and second brush heads, respectively.

24. The brush tip of claim 21 wherein said first and second sets of cleaning members extending from said first and second brush heads, respectively, at an angle.

25. The brush tip of claim 21 wherein said first set of cleaning members extending substantially vertically from said first brush head and said second set of cleaning members extending from said second brush head at an angle away from said first brush head.

26. The brush tip of claim 21 wherein said cleaning member is selected from the group consisting of bristle, tuft of bristles and rubber-like extension.

27. The brush tip of claim 1 further comprising a cover that correspondingly mates with said housing for enclosing said elongated shaft.

28. The brush tip of claim 1 further comprising means for retaining said first brush head in said first opening of said housing while allowing said first brush head to freely rotate about said first axis of rotation.

29. The brush tip of claim 1 further comprising means for retaining said second brush head in said second opening of said housing while allowing said second brush head to freely rotate about said second axis of rotation.

30. The brush tip of claim 1 wherein said housing further having a curve groove, further comprising a third brush head supported by said housing in said curve groove, and said second brush head further encircling said third brush head.

31. The brush tip of claim 30 wherein said second brush head comprises a generally elliptic cylindrical body having a generally central and elliptical aperture where said first brush head nests therein and a generally rectangular opening where said third brush head nests therein.

32. The brush tip of claim 31 further comprising means for moving said third brush head along said curve groove and for pivoting said third brush head towards and away from said generally central and elliptical aperture of said generally elliptic cylindrical body.

33. The brush tip of claim 32 wherein said third brush head having a generally rectangular prism shape tapered body, and said moving and pivoting means comprises a pair of channels on opposite walls of said generally rectangular opening, a pin extending from a lower surface of said body of said third brush head for engaging said curve groove of said housing, and a protrusion extending from each of the opposite side walls of said body of said third brush head for engaging said pair of channels on the opposite walls of said generally rectangular opening.

34. The brush tip of claim 30 wherein said third brush head having a third set of cleaning members extending therefrom.

35. The brush tip of claim 34 wherein said cleaning member is selected from the group consisting of bristle, tuft of bristles and rubber-like extension.

36. The brush tip of claim 1 wherein said cleaning member is selected from the group consisting of bristle, tuft of bristles and rubber-like extension.

37. A brush tip for a motorized toothbrush, comprising:
- a housing having a first opening defining a first axis of rotation, a second opening defining a second axis of rotation different from said first axis of rotation, and a cavity;
- a first brush head supported by said housing in said first opening for rotation about said first axis of rotation, said first brush head comprises a generally cylindrical body having a curve side wall, along a portion of said curve side wall is a first set of elongated gear teeth having axes parallel to the central axis of said cylindrical body;
- a second brush head supported by said housing in said second opening for rotation about said second axis of rotation, said second brush head encircling said first brush head, said second brush head comprises a generally elliptic cylindrical body having a generally central and elliptical aperture where said first rush head nests therein and a concave side wall in said elliptical aperture, along a portion of said concave side wall is a second set of elongated gear teeth having axes parallel to the central axis of said elliptic cylindrical body; and
- an elongated shaft supported by said housing in said cavity for rotation about a shaft axis, engaging said second brush head to drive said first and second brush heads;
- wherein each of said first and second set of gear teeth having equal pitch circle radii and interact with each to counter-rotate and accelerate said first and second brush heads at equal angular acceleration.

38. A brush tip for a motorized toothbrush, comprising:
- a housing having a first opening defining a first axis of rotation, a second opening defining a second axis of rotation different from said first axis of rotation, and a cavity;
- a first brush head supported by said housing in said first opening for rotation about said first axis of rotation, said first brush head comprises a generally cylindrical body having a curve side wall, along a portion of said curve side wall is a first set of elongated gear teeth having axes parallel to the central axis of said cylindrical body;
- a second brush head supported by said housing in said second opening for rotation about said second axis of rotation, said second brush head encircling said first brush head, said second brush head comprises a generally elliptic cylindrical body having a generally central and elliptical aperture where said first rush head nests therein and a concave side wall in said elliptical aperture, along a portion of said concave side wall is a second set of elongated gear teeth having axes parallel to the central axis of said elliptic cylindrical body; and
- an elongated shaft supported by said housing in said cavity for rotation about a shaft axis, engaging said second brush head to drive said first and second brush heads;

wherein each of said first and second set of gear teeth having different pitch circle radii and interact with each to counter-rotate and accelerate said first and second brush heads at different angular acceleration.

39. A brush tip for a motorized toothbrush having a toothbrush motor, comprising:

a first set of cleaning members extending from a first brush head, distal ends of said first set of cleaning members forming a circular pattern;

a second set of cleaning members extending from a second brush head, distal ends of said second set of cleaning members forming a non-circular pattern, said second brush head encircling said first brush head; and means for counter-rotating said first set of cleaning members about a first axis of rotation and said second set of cleaning members about a second axis of rotation different from said first axis of rotation, in response to motion produced by said toothbrush motor.

40. The brush tip of claim 39, wherein said motorized toothbrush having a shaft that produces oscillating rotational motion about said shaft, and wherein said counter-rotating means transmits said motion to said first and second sets of cleaning members.

41. The brush tip of claim 39 wherein said counter-rotating means further comprising means for accelerating said first and second sets of cleaning members at equal angular acceleration.

42. The brush tip of claim 39 wherein said counter-rotating means further comprising means for accelerating said first and second sets of cleaning members at different angular acceleration.

43. The brush tip of claim 39 wherein said cleaning member is selected from the group consisting of bristle, tuft of bristles and rubber-like extension.

* * * * *

UNITED STATES PATENT AND TRADEMARK OFFICE
CERTIFICATE OF CORRECTION

PATENT NO.        : 8,302,238 B2
APPLICATION NO.   : 12/460625
DATED             : November 6, 2012
INVENTOR(S)       : Ladislau Biro and Howard Cohen It is certified that error appears in the above-identified patent and that said Letters Patent is hereby corrected as shown below:

Title page, item [54] and in the specification, col. 1,
Title: The title "Motorized Toothbrush Tip Having Inner and Other Heads Counter Around Different Axes" should be corrected to read "Motorized Toothbrush Tip Having Inner and Outer Heads Counter Rotating Around Different Axes"

Signed and Sealed this
Fourteenth Day of January, 2014

Michelle K. Lee
*Deputy Director of the United States Patent and Trademark Office*